United States Patent [19]

Hui et al.

[11] Patent Number: 5,315,015

[45] Date of Patent: May 24, 1994

[54] COMPOUNDS HAVING IMPROVED FLUORESCENCE IN FLUORESCENCE POLARIZATION IMMUNOASSAYS AND IMMUNOASSAYS UTILIZING SAME

[75] Inventors: Raymond A. Hui, Lyndhurst, N.J.; Kathryn S. Schwenzer, Yardley, Pa.

[73] Assignee: Hoffmann-La Roche Inc., Nutley, N.J.

[21] Appl. No.: 974,397

[22] Filed: Nov. 10, 1992

[51] Int. Cl.$^5$ ............................................. C07D 493/10
[52] U.S. Cl. .................................... 549/223; 549/224; 549/225; 549/226; 549/227
[58] Field of Search ............... 549/223, 225, 224, 226, 549/227

[56] References Cited

U.S. PATENT DOCUMENTS

| | | | |
|---|---|---|---|
| 4,255,329 | 3/1981 | Ullman | 260/239 D |
| 4,476,228 | 10/1984 | Huchzermeier et al. | 436/500 |
| 4,476,229 | 10/1984 | Fino et al. | 436/500 |
| 4,668,640 | 5/1987 | Wang et al. | 436/536 |

OTHER PUBLICATIONS

Burchiel, S., "Methods in Enzymology," vol. 121, Chap. 57, pp. 596–615, Academic Press, New York (1986).

Cohler and Milstein, *Nature*, 256, pp. 495–497 (1975).
Colbert, et al., *Analyst*, 112 pp. 1483–1486 (1987).
Dandliker, et al., *Immunochemistry*, 10, pp. 219–227 (1973).
Fairclough & Cantor, *Methods in Enzymology*, 48, pp. 347–379 (1978).

*Primary Examiner*—Richard L. Raymond
*Attorney, Agent, or Firm*—George M. Gould; George W. Johnston; John P. Parise

[57] ABSTRACT

Compounds of the formula

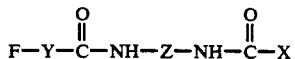

wherein F is a fluorescing compound; Y is —NH— or a single covalent bond; Z is a straight or branched alkylene chain of 2 to 10 carbon atoms which is substituted by at least one hydrophilic group; Q is oxygen or sulfur; and X is a ligand-analog, the ligand-analog capable of being recognized by an antibody specific to the corresponding ligand. These compounds have improved properties in fluorescence polarization immunoassays by possessing either a better intensity and/or a larger span.

13 Claims, No Drawings

COMPOUNDS HAVING IMPROVED FLUORESCENCE IN FLUORESCENCE POLARIZATION IMMUNOASSAYS AND IMMUNOASSAYS UTILIZING SAME

Field of the Invention

The present invention relates to compounds which possess improved fluorescence in fluorescence polarization immunoassays and also to immunoassays utilizing the compounds.

Background of the Invention

Competitive binding immunoassays are well known and can be utilized for quantitatively detecting ligands in a test sample. In general, the procedure for the immunoassays involves labeling an analog of the ligand of interest with, for example, a fluorescent label, or a radio-label, e.g., tritium, $^{32}P$, $^{125}I$ or $^{14}C$. The labeled analogs, which are conventionally termed "tracers", are mixed in a sample suspected of containing the ligand of interest. Intermixed with the sample is an antibody which is capable of recognizing both the ligand and the ligand analog. In the sample mixture, the ligand and ligand analog compete for the limited number of antibody binding sites. The amount of tracer-antibody complexes measured in the sample is an inverse function of the amount of ligand in the sample.

When the tracer carries a fluorescent label, the tracer-antibody complexes can be detected using conventional fluorescence polarization immunoassay (FPIA) techniques. In a general sense, when a fluorescent-labeled tracer is excited by linearly polarized light, the observed polarization of the emitted light is inversely related to the rate of rotation of the tracer. By comparison to bound tracer molecules, the unbound tracer molecules rotate more rapidly and this causes the emitted light to be depolarized to a greater degree than that from tracer molecules bound to antibody. The extent of polarized fluorescence emission may be easily measured by FPIA methods and will be proportional to the amount of tracer-antibody complexes present in the sample. Thus, FPIA can be used to quantitatively measure the amount of tracer-antibody conjugates produced in a competitive binding immunoassay.

A variety of fluorescent-labeled tracers useful in FPIA are known in the art. For example, U.S. Pat. No. 4,668,640 describes carboxyfluorescein derivatives and U.S. Pat. No. 4,255,329 describes linking groups connecting the ligand analog to the fluorescent label. Such linking groups are described generally as carboxymethoxyimino, acetylglycyl, butyrylglycyl, glycyl, crotonylglycyl, acetyl, crotonyl, succindioyl, and oxalyl.

SUMMARY OF THE INVENTION

The present invention relates to tracer compounds of the formula:

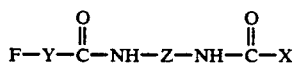

wherein F is a fluorescent compound; Y is —NH— or a single covalent bond; Z is a straight or branched chain alkylene linking group of 2 to 10 carbon atoms which is substituted by at least one polar hydrophilic group; Q is oxygen or sulfur; and X is a ligand-analog, the ligand-analog capable of being recognized by an antibody specific to the corresponding ligand.

The present invention relates further to a method for detecting ligands in a sample of biological fluid, including, for example, urine, plasma, serum, spinal fluid, and amniotic fluid. The method comprises the steps of intermixing the sample with a compound of the formula I and with an antibody specific to both the ligand and the ligand-analog; and measuring the concentration of the ligand in said sample by fluorescence polarization techniques.

DETAILED DESCRIPTION OF THE INVENTION

The present invention pertains to tracer compounds of the formula:

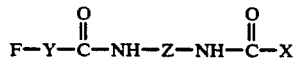

wherein F is a fluorescent compound; Y is —NH— or a single covalent bond; Z is a straight or branched chain alkylene linking group of 2 to 10 carbon atoms which is substituted by at least one polar hydrophilic group; Q is oxygen or sulfur; and X is a ligand-analog, the ligand-analog capable of being recognized by an antibody specific to the corresponding ligand.

As used herein, the term "fluorescent group" means any conventional compound which when excited by polarized light of suitable wavelength, will emit fluorescence having a degree of polarization in a general sense inversely related to its rate of rotation. See, for example, J. R. Lakowicz in "Principles of Fluorescence Spectroscopy," Plenum Press, 1983. Typical fluorescing compounds represented by F in formula I, and which are suitable for use in the present invention include, for example, fluoresceinyl, substituted fluoresceinyl, rhodaminyl, substituted rhodaminyl, and naphthofluoresceinyl. Preferred are 5-fluoresceinyl or 6-fluoresceinyl. However, any compound having the above described property is suitable for use in the present invention.

As used herein, the term "ligand" means any conventional protein-free low molecular weight compound having biological interest and the presence of which in a sample of biological fluid can be determined by using the present invention, such as drugs of abuse and therapeutic compounds. See, for example, U.S. Pat. Nos. 4,255,329; 4,668,640; Colbert et al, Analyst, 112 (1987), 1483–1486; Dandliker et al, Immunochemistry, 1973, 10, 219–227. See also for example, Fairclough and Cantor, Methods in Enzymology, 48 (1978), pp 347–379. Typical of the ligands determinable in a sample using the present invention include, but are not limited to, tetrahydrocannabinoids, opiates, N-acetylprocainamide, carbamazepines, phenytoins, and their respective metabolites.

What is meant by "protein-free low molecular weight compound" is an organic compound typically of molecular weight less than 2000 which possesses at least one polar functionality, and which may or may not incorporate amino acid moieties within its structure, but which by itself is generally incapable of eliciting an immune response if introduced to an animal to which it is foreign.

What is meant by the term "ligand-analog" is a compound which is sufficiently similar in chemical structure to the ligand, such that an antibody which recognizes the ligand with good specificity will also recognize the ligand-analog also with good specificity. As an example, X in formula I may be a tetrahydrocannabinoid analog such as 6a,7,10,10a-tetrahydro-1-hydroxy-6,6-dimethyl-3-pentyl-6H-dibenzo[b,d]pyran-9-yl or 6a,7,8,10a-tetrahydro-1-hydroxy-6,6-dimethyl-3-pentyl-6H-dibenzo-[b,d]pyran-9-yl.

The linking group represented by Z in formula I, i.e., "straight or branched chain alkylene linking group of 2 to 10 carbon atoms which is substituted by at least one polar hydrophilic group" includes ethylene, propylene, butylene, pentylene, hexylene, heptylene, octylene, nonylene, decylene, and all functional isomers thereof (e.g. isopropylene, t-butylene, etc.), substituted by at least one polar hydrophilic group.

What is meant by "polar hydrophilic group" is a functional group comprising at least two atoms, of which at least one is a heteroatom (such as oxygen, nitrogen, sulfur, or phosphorus) and which possesses the property of polarization of charge either within itself or between itself and its point of attachment to the rest of the molecule (such as the alkylene linker of the present invention) and is capable of hydrogen bonding to, typically, water molecules, or to other polar groups; and as classically described and discussed by, e.g., Linus Pauling in "The Nature of the Chemical Bond," Cornell University Press, 3rd Ed., 1960, Chp. 12. Polar hydrophilic groups suitable for the invention include, but are not limited to, groups such as hydroxy, carboxy, carboxylate ester (—C(O)OR', R'=alkyl), carbamoyl, thiocarbamyl, amino (primary, secondary, or tertiary), acylamino, sulfino, sulfo, sulfamyl, phosphono, as well as both hydroxyalkoxy and aminoalkoxy, each having 1 to 8 carbon atoms. Preferred polar hydrophilic groups are hydroxy, carboxy, carboxylate ester, amino (primary, secondary, or tertiary), acylamino, hydroxyalkoxy of 1 to 8 carbon atoms, and aminoalkoxy of 1 to 8 carbon atoms.

The term "substituted", as used herein, means that at least one hydrogen atom of the alkylene linking group is replaced by a polar hydrophilic group.

What is meant by the term "alkyl" is any straight or branched aliphatic carbon group of the formula —$C_nH_{2n+1}$, wherein n is an integer from 1 to 8.

By "alkoxy" what is meant is any straight or branched aliphatic carbon group of the formula —O—$C_mH_{2m+1}$ wherein m is an integer from 1 to 8.

The term acylamino means groups having the formula —N($R_1$)—C(O)—$R_2$ where $R_1$ is H or alkyl, and $R_2$ is H or alkyl or alkoxy.

Antibodies which are used in the competitive binding assays of the invention can be generated and purified using conventional, well-known methods. Such methods are described for example, in Cohler & Milstein, Nature, 256, pp. 495–497 (1975); "Antibodies-A Laboratory Manual", E. Harlow & D. Lane, Coldspring Harbor Laboratory, pp. 55–144 (1988); C. Williams & M. Chase, in "Methods in Immunology & Immunochemistry," Academic Press, New York, Vol. 1, Chap. 3, (1967); and S. Burchiel, in "Methods in Enzymology," Vol. 121, Chap. 57, pp. 596–615, Academic Press, New York (1986). In general, an immunogen is administered to an animal in order to elicit an immune response against the immunogen. Antibodies specific to both the ligand of interest and to the ligand-analog can be raised by using an immunogen having the same general structure of the ligand and ligand analog. Polyclonal antibodies generated against the immunogen are obtained from the animal antisera and are then purified using well-known methods. Monoclonal antibodies against the immunogen can be obtained from hybridoma cells using well-known methods.

Suitable immunogens for raising polyclonal antibodies to tetrahydro-cannabinoid ligands and tetrahydrocannabinoid ligand-analogs include, but are not limited to, compounds of the formula:

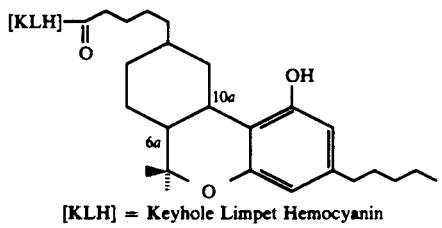

[KLH] = Keyhole Limpet Hemocyanin

Sheep or goats can be immunized with the above compound and antisera can be obtained by methods well known in the art.

Generation of monoclonal antibodies to tetrahydrocannabinoid ligands and tetrahydrocannabinoid ligand-analogs can be affected using the above immunogen wherein the KLH is replaced by bovine thyroglobulin. Mice can then be immunized with the immunogen and monoclonal antibodies obtained after the requisite clonal fusions are performed using methods well known in the art.

The above immunogens are illustrative examples only, and any protein or polyamino acid may also be used as the carrier in a manner apparent to a person skilled in the art.

Preferred linking groups of the invention are 2-hydroxy propylene, carboxyethylene, 1-carboxy pentylene, 1-ethylcarboxylate pentylene, and 1-carboxybutylene.

Preferred tracers are those wherein Q is oxygen and Z is 2-hydroxy propylene. Further preferred tracers are those having the following formulas:

Tracer Ia

-continued
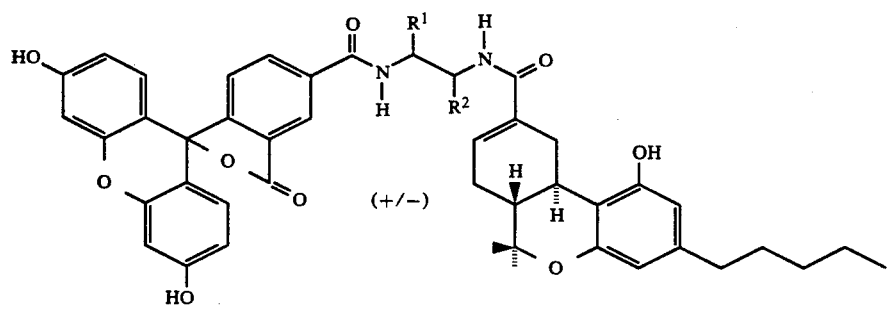
R¹ = H, R² = COOH or
R¹ = COOH, R² = H
Tracer Ib
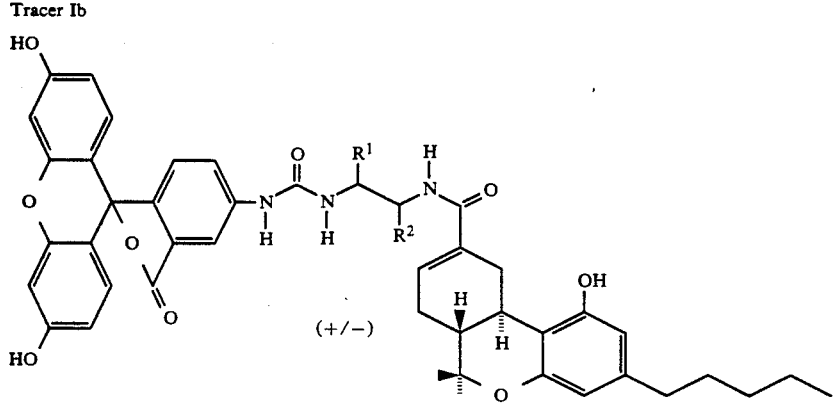
R¹ = H, R² = COOH or
R¹ = COOH, R² = H
Tracer Ic
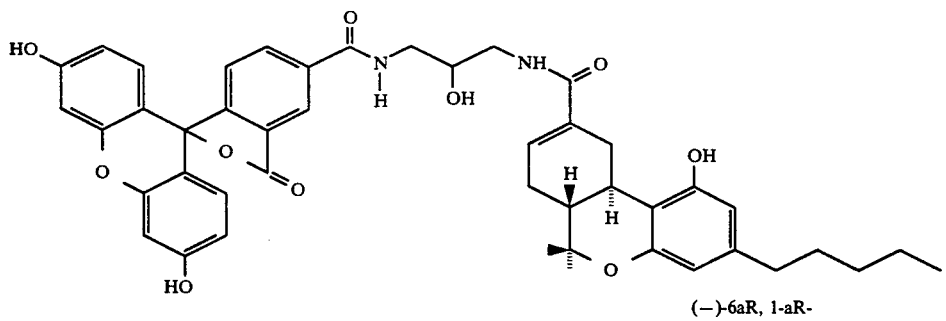
(−)-6aR, 1-aR-
Tracer Id
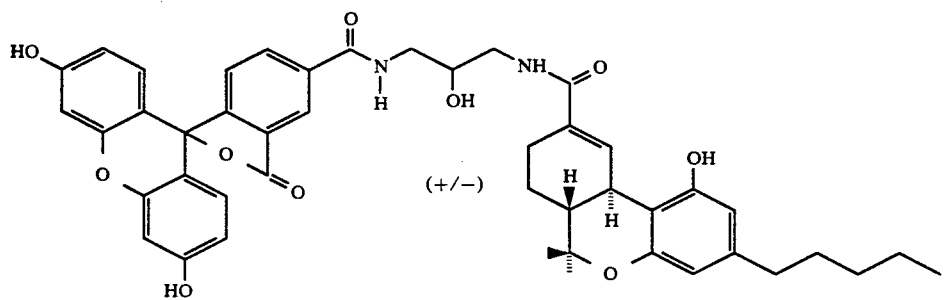
Tracer Ie -continued
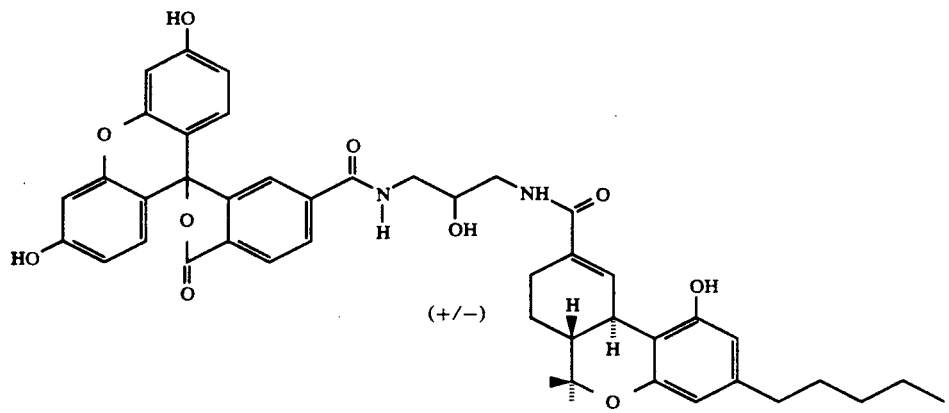
Tracer If
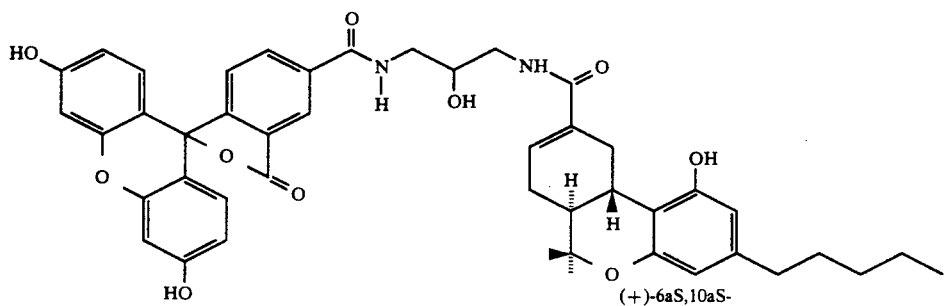
(+)-6aS,10aS-
Tracer Ig
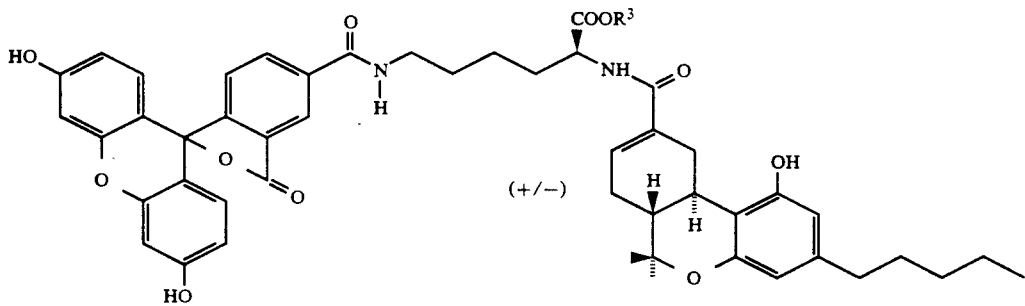
$R^3$ = H or $CH_2CH_3$
Tracer Ih
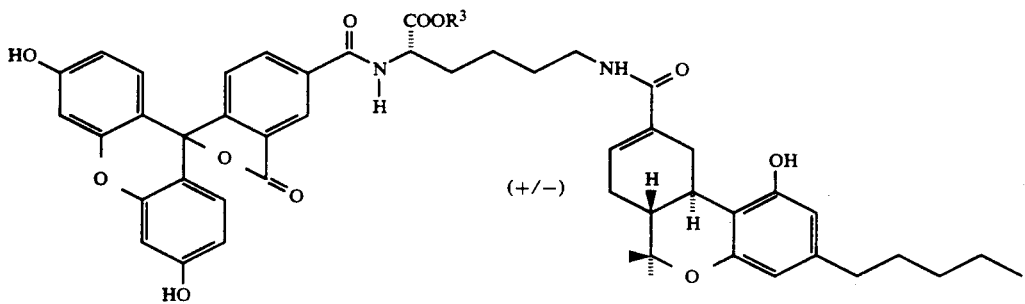
$R^3$ = H or $CH_2CH_3$
Tracer Ii

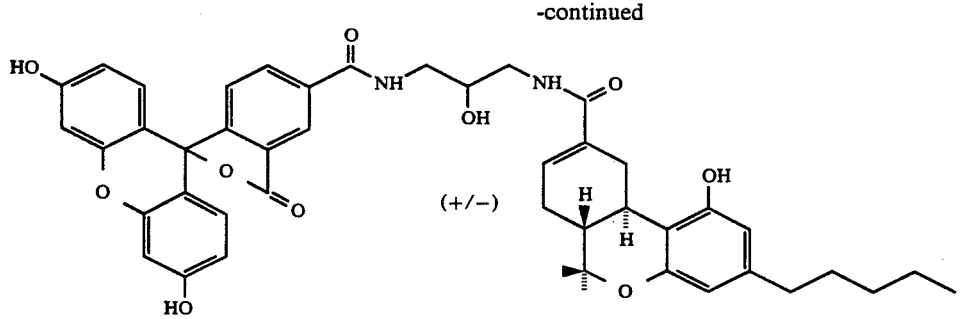
Tracer Ij
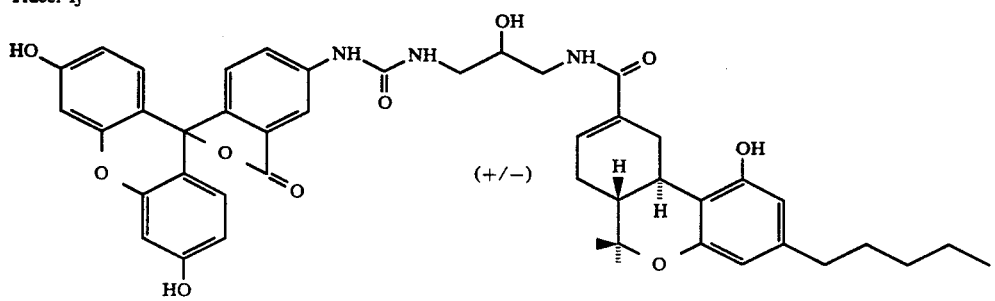
Tracer Ik
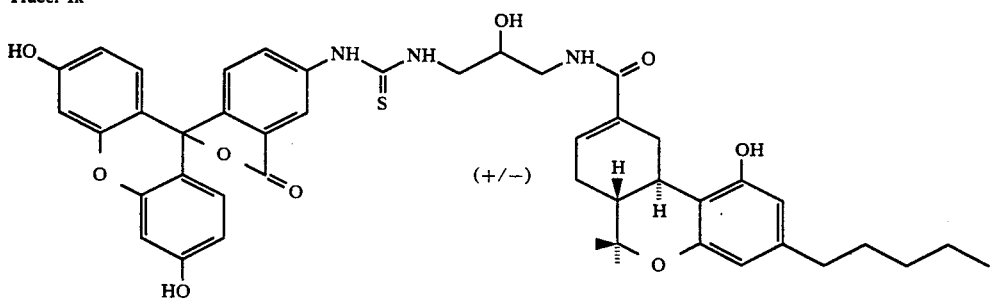
Tracer Il
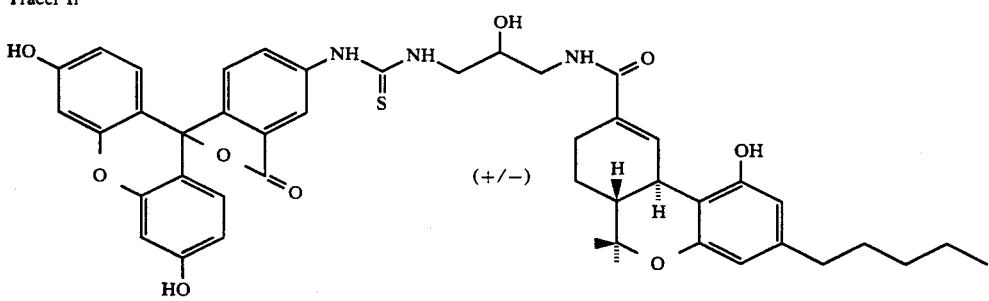
Tracer Im
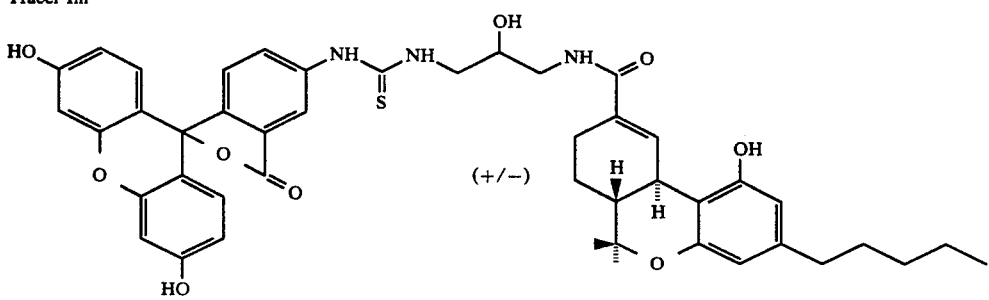
Tracer Ic is a (−)-6aR, 10aR isomer in the tetrahydrocannabinoid (THC) portion, and tracer Ii is racemic in the THC portion and is a 1:1 mixture of tracers Ic and If.

The tracers of formula I provide improved properties over compounds known in the art by possessing better intensity and by providing a larger span when utilized in FPIAs. The span is a measure of the total decrease in observed mP (fluoresence polarization) units with increasing concentrations of added ligand. The larger the span, the better the precision of measurement.

The intensity is a measure of the strength of the signal above the background. Thus, the higher the intensity, the more accurate the measurement. When the overall span is large, small changes in the concentration of the ligands or tracers in the assay produce a relatively large change in the observed mP value. This leads to greater sensitivity and precision in measuring the small quantities of ligands (drug-analyte) typically present in clinical samples. When the intensity of the tracer is high, the signal to noise ratio is high. This allows a reduction in the amount of tracer needed to be used in the assay to generate a signal with a good signal to noise ratio, as compared with a tracer that demonstrates low intensity. Such reduction in the amount of tracer used in the assay in a general sense means that comparatively fewer tracer molecules (each containing the ligand-analog as part of its structure) are available to compete with the ligand for binding to the limited amount of antibody present in the sample being analyzed. This in turn contributes to a steeper decrease in the observed fluorescence polarization with an increase of ligand present, especially at low concentrations of ligand. This helps in increasing the span of the standard curve and helps in increasing the sensitivity of the immunoassay.

The tracers of the present invention can be prepared by following the general reaction schemes 1–7 below, and the Examples which follow. In general, the tracers can be prepared by reacting either 6a,7,10,10a-tetrahydro-1-hydroxy-6,6-dimethyl-3-pentyl-6H-dibenzo[b,d]pyran-9-carboxylic acid or 6a,7,8,10a-tetrahydro-1-hydroxy-6,6-dimethyl-3-pentyl-6H-dibenzo[b,d]pyran-9-carboxylic acid with N-hydroxysuccinimide using a carbodiimide coupling agent. The resulting compound can then be reacted with a diamino linker compound, and subsequently reacted with 5- or 6-carboxyfluorescein N-hydroxysuccinimide ester, or with 5- or 6-isocyanatofluorescein, or with 5- or 6-isothiocyanatofluorescein.

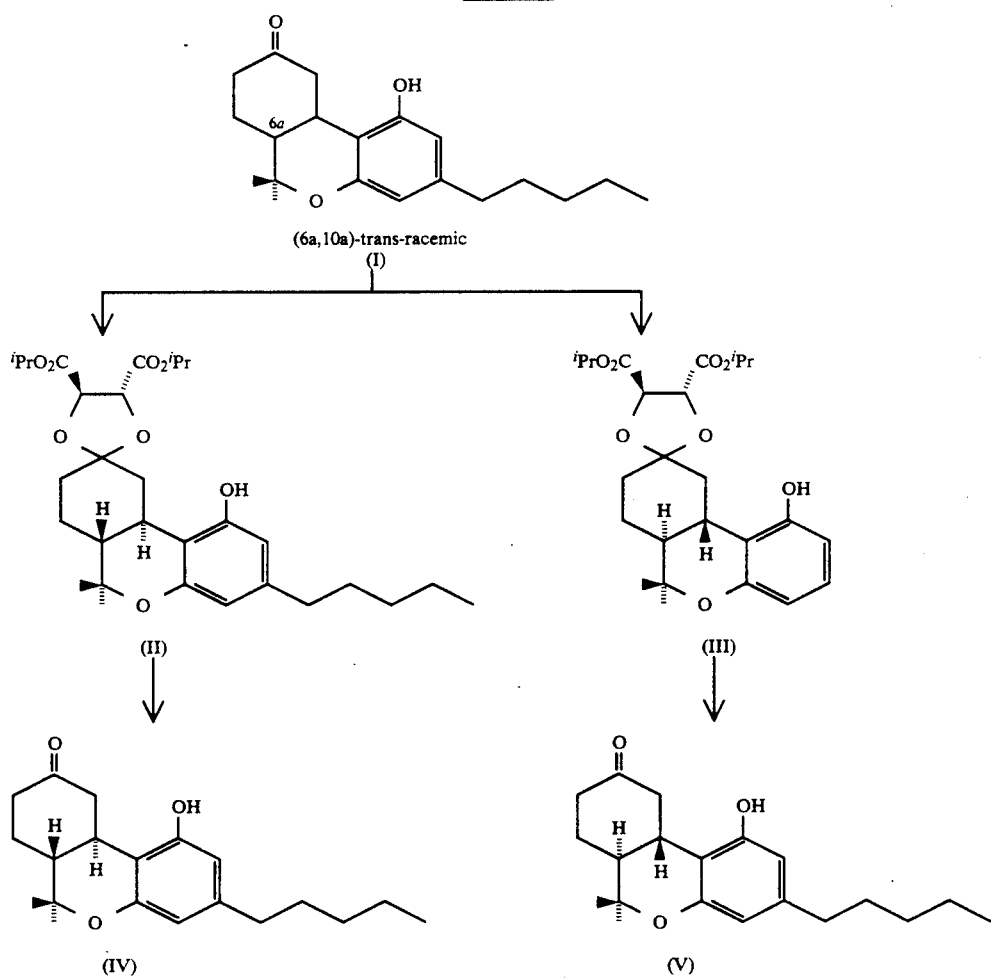

Scheme 1

Scheme 2
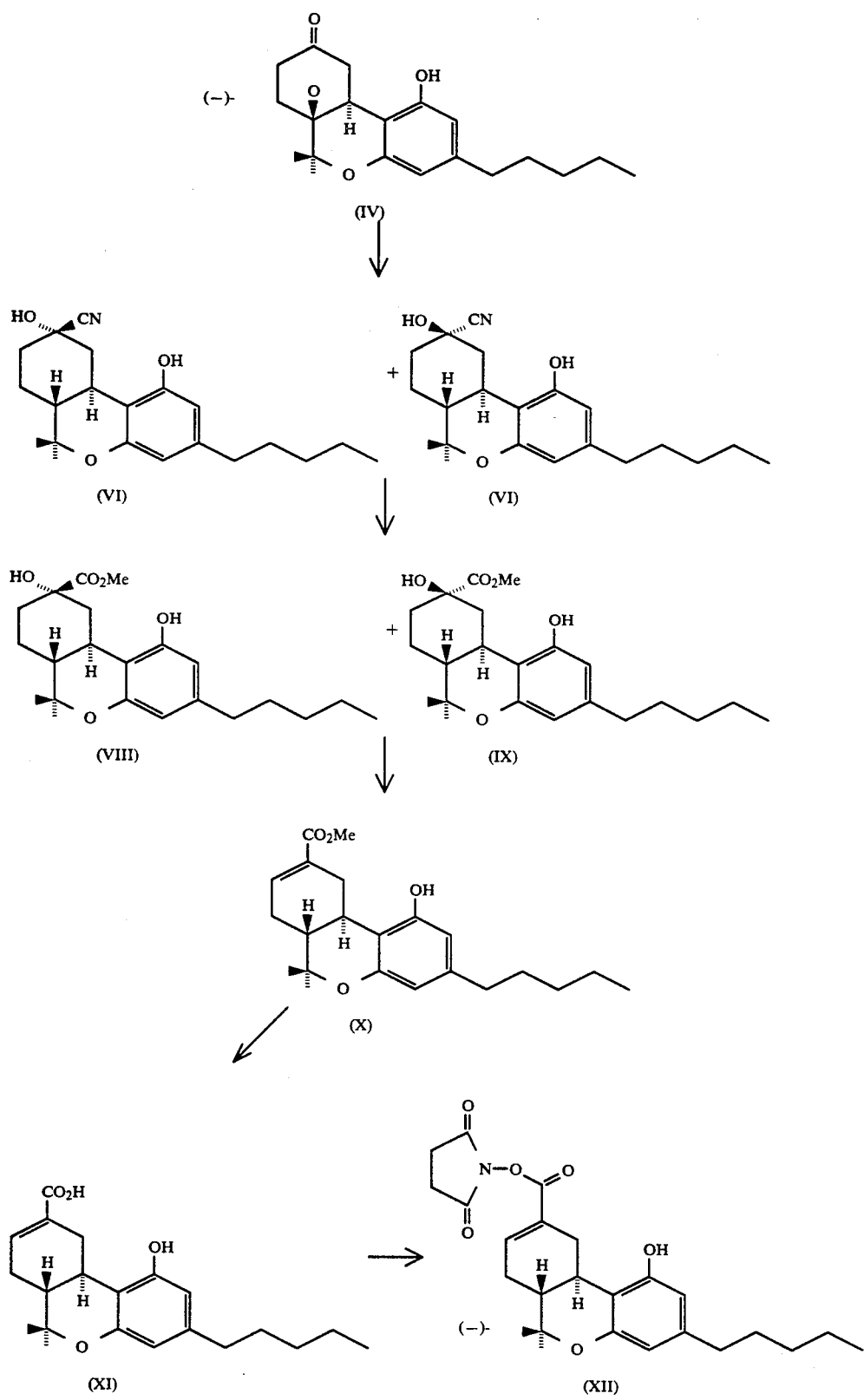

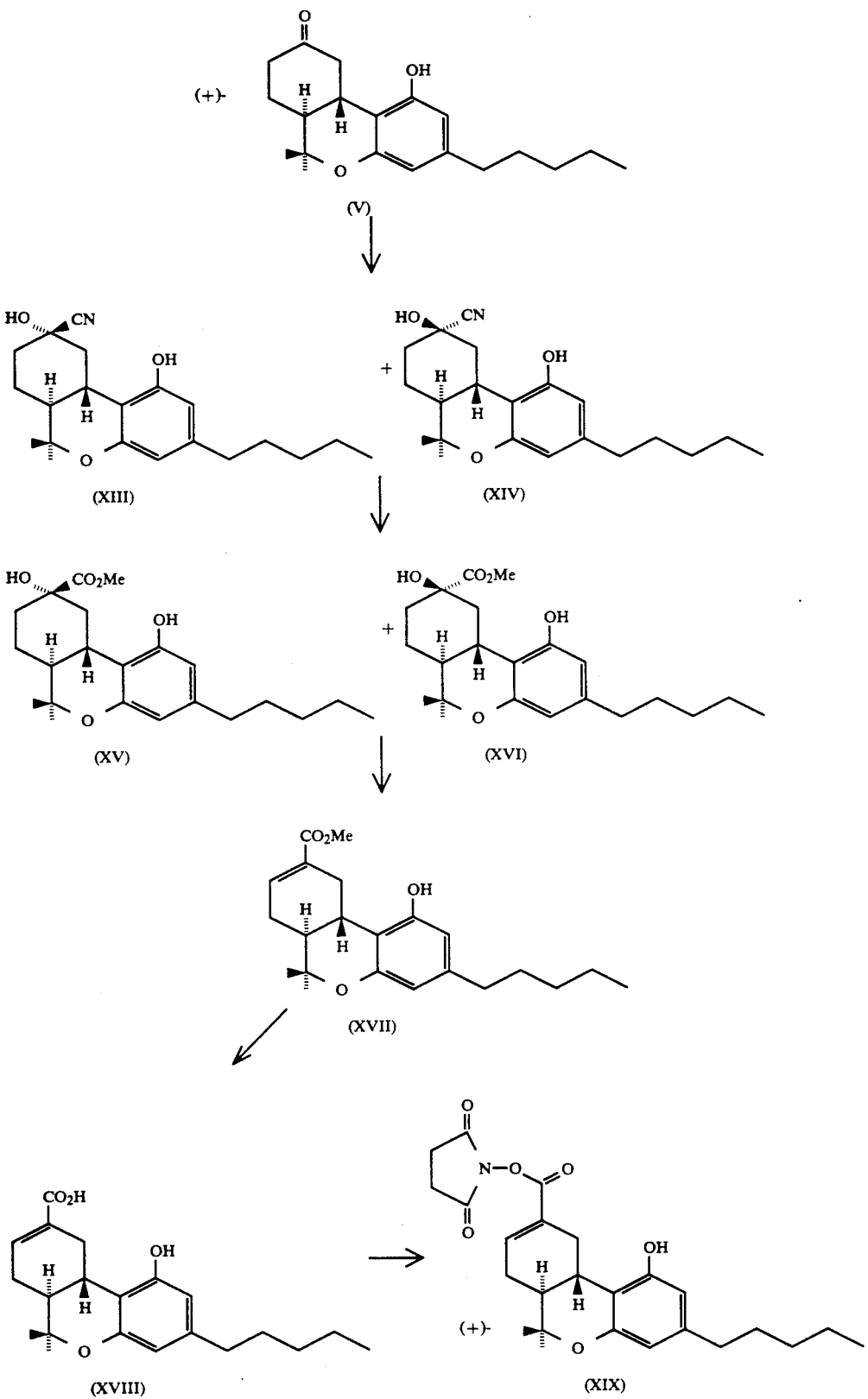
Scheme 3

Scheme 4a
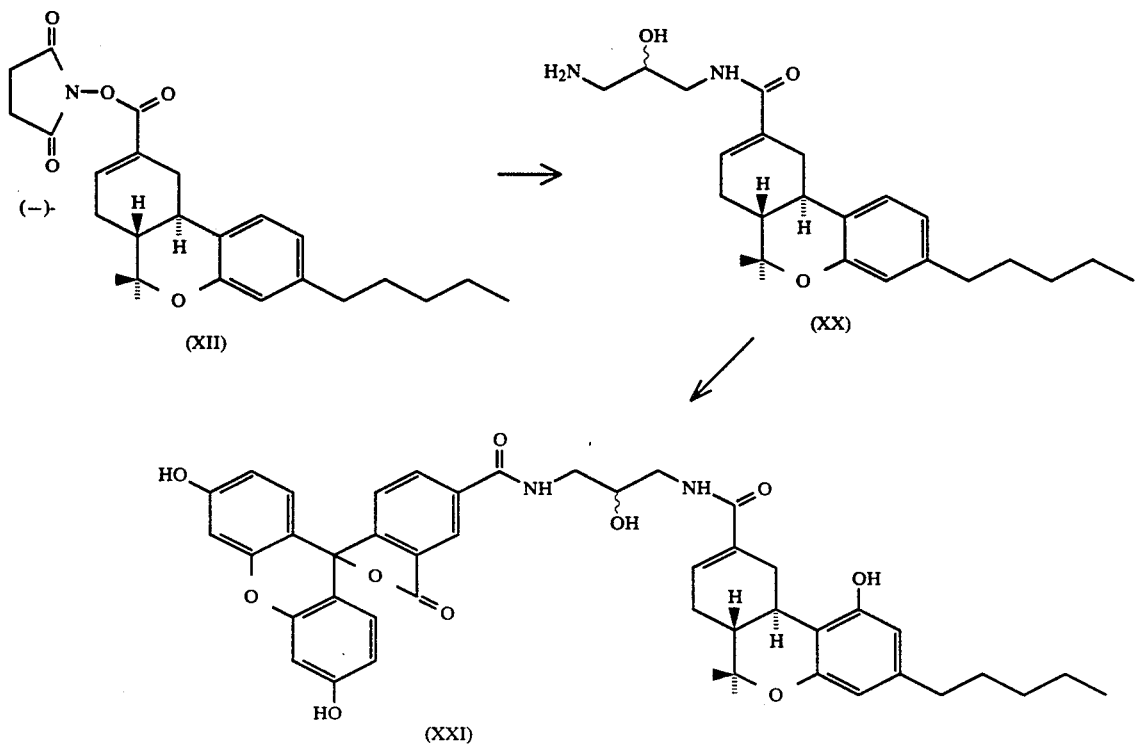
Scheme 4b
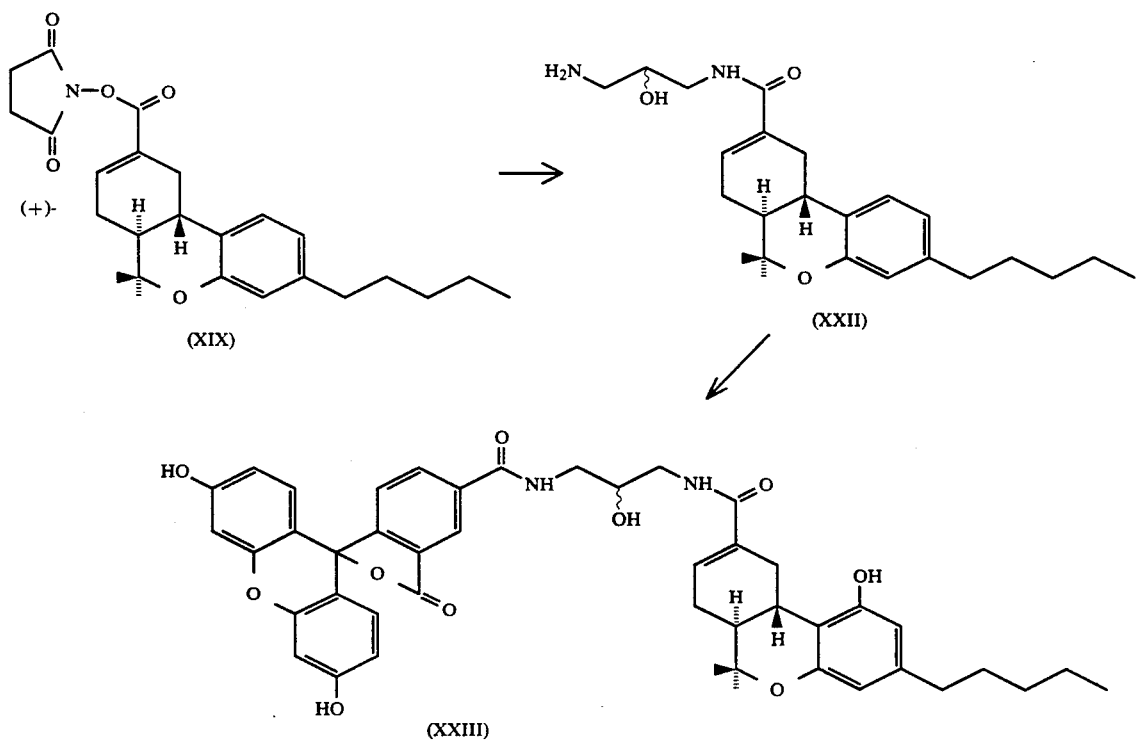

Scheme 5

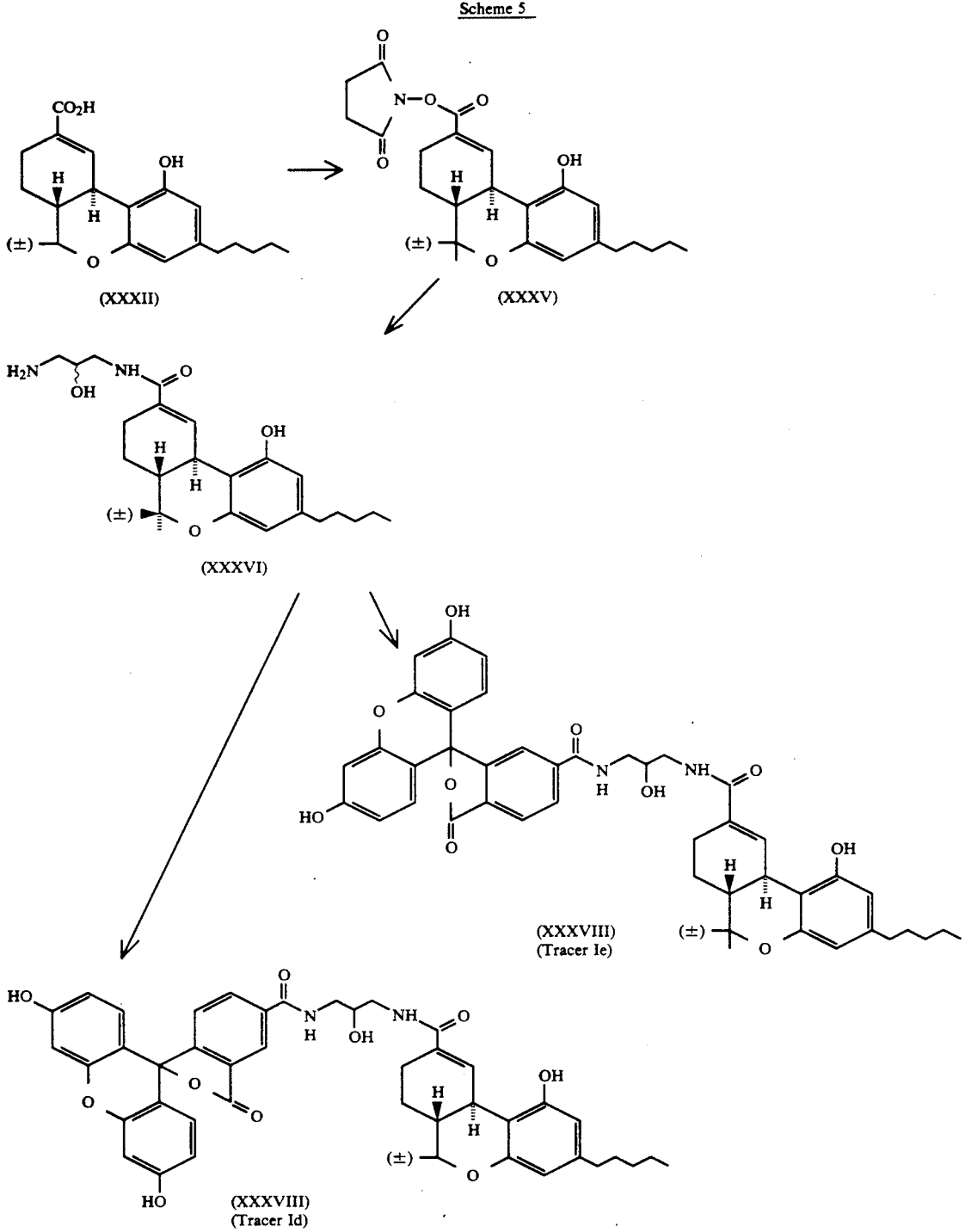

The following Examples are illustrative of the invention and are not to limit the scope thereof. Except where noted, all Examples have been carried out as written. As used in the Examples, "work-up" refers to quenching or stopping of the reaction and initial isolation of products from the reaction by methods well-known to practicers of organic chemistry and "room-temperature" means about 23° C. In addition, all solvent ratios are expressed as volume ratios.

EXAMPLE 1

Resolution of (trans-racemic)-6a,7,10,10a-tetrahydro-1-hydroxy-6,6-dimethyl-3-pentyl-6H-dibenzo[b,d]pyran-9(8H)-one (I)

Referring to scheme 1, to a solution of 5.00 g, 0.016 mol, of (trans-racemic)-6a,7,10,10a-tetrahydro-1-hydroxy-6,6-dimethyl-3-pentyl-6H-dibenzo[b,d]pyran-9(8H)-one (Fahrenholtz, Lurie and Kierstead, J. Am. Chem. Soc., 1967, 89, 5934; McNally, Schwartz and Usategui, U.S. Pat. No. 4,833,073) in 100 mL of dry toluene was added 3.80 g, 0.017 mol, 1.05 equiv, of (+)-diisopropyl L-tartrate (Aldrich) and 0.25 g of p-toluenesulfonic acid monohydrate (MCB). The solution was boiled under reflux with collection of water formed in the reaction in a Dean-Stark trap. After 18 h the brown reaction mixture was cooled to room temperature, concentrated in vacuo to a volume of about 20 mL and passed through a plug of silicagel 60 (3.5 cm depth×4.5 cm diameter) in a sintered glass funnel, washing through with 100 mL of toluene followed by 100 mL of hexanes and the washings combined (fraction 1). The silicagel plug was then eluted further with 200 mL of diethyl ether (fraction 2) plus an additional 200 mL of diethyl ether (fraction 3). Evaporation in vacuo of fraction 1 then afforded 5.52 g of a foam shown by TLC analysis to contain mainly the (6aS,10aS)-isomer (III) together with the (6aR,10aR)-isomer (II). Evaporation in vacuo of fraction 2 gave 3.72 g of a foam shown by TLC analysis to contain mainly (II), together with (III). The material from fractions 1 and 2 were combined and subjected to silicagel chromatography on a Waters Prep 500A LC System, gradient elution with EtOAc (ethylacetate)-hexanes (5:95 to 15:85 volume ratio) with rechromatography of mixed fractions, to give the less polar (6aS,10aS)-isomer (III) (2.92 g, 35%) as an off-white foam, the analytical sample of which had $[\alpha]_D-53°$ (CHCl$_3$), M+ 532.3013 (Calc 532.3036); and the more polar (6aR,10aR)-isomer (II) (2.31 g, 27%) as an off-white foam, the analytical sample of which had $[\alpha]_D-56°$ (CHCl$_3$), M+ 532.3004 (Calc 532.3036); together with 0.79 g, 9%, of less pure (II).

EXAMPLE 2

(6aR,10aR)-6a,7,10,10a-Tetrahydro-1-hydroxy-6,6-dimethyl-3-pentyl-6H-dibenzo[b,d]pyran-9(8H)-one (IV)

With continued reference to scheme 1, to a solution of the tartrate ketal (II) (0.76 g, 1.43 mmol) in purified tetrahydrofuran (THF) (40 mL) under argon was added 3N aqueous perchloric acid (25 mL) and the clear solution heated at 70° C. under a reflux condenser for 17.5 h. The cooled (room temperature), pale yellow solution was diluted with water (40 mL), solid NaHCO$_3$ cautiously added (effervescence) to saturation, and the resulting solution extracted with four portions of EtOAc. The combined organic layers were washed with saturated NaCl, dried over MgSO$_4$ and evaporated in vacuo to give 540 mg of a discolored crystalline solid. This was digested at room temperature with methylene chloride (about 5 mL) and the resulting solution containing white solids applied to the top of a plug of silicagel 60. The silica was washed through with 250 mL of EtOAc-hexanes (3:7) and the pale yellow filtrates concentrated in vacuo to afford 441 mg of a pale yellow foam. This was subjected to medium pressure liquid chromatography (MPLC) on silica, eluting with EtOAc-hexanes (3:7) to give 400 mg, 89%, of the pure (6aR,10aR)-ketone (IV) as a white crystalline foam: mp 114°-117° C.; $[\alpha]_D$ −91° (CHCl$_3$), M+ 316.2032 (Calc 316.2038); Anal. Calc for C$_{20}$H$_{28}$O$_3$: C, 75.91; H, 8.92. Found: C, 75.96; H, 8.81%.

EXAMPLE 3

(6aS,10aS)-6a,7,10,10a-Tetrahydro-1-hydroxy-6,6-dimethyl-3-pentyl-6H-dibenzo[b,d]pyran-9(8H)-one (V)

In a similar manner to the procedure described for (IV) and shown in scheme 1, hydrolysis of (III) (0.60 g, 1.13 mmol) in distilled THF (10 mL) with 3N HClO$_4$ (10 mL) at 70° C. under argon for 3 h gave, after workup, 326 mg of a light yellow-brown gum. This was subjected to preparative TLC on silica, eluting with EtOAc-hexanes (3:7) to give, from the main product band, 220 mg, 62%, of the (6aS,10aS),-ketone shown in formula (V). The analytical sample was recrystallized from hexanes at −20° C. to give colorless needles: mp 115°-117° C.; $[\alpha]_D$ +92° (CHCl$_3$), M+ 316.2034 (Calc 316.2038); Anal. Calc for C$_{20}$H$_{28}$O$_3$: C, 75.91; H, 8.92. Found: C, 75.70; H, 9.09%.

EXAMPLE 4

(6aR,9S,10aR)-6a,7,8,9,10,10a-Hexahydro-1,9-dihydroxy-6,6-dimethyl-3-pentyl-6H-dibenzo[b,d]pyran-9-carbonitrile (VI) and (6aR,9R,10aR)-6a,7,8,9,10,10a-hexahydro-1,9-dihydroxy-6,6-dimethyl-3-pentyl-6H-dibenzo[b,d]pyran-9-carbonitrile (VII)

Referring to scheme 2, to a solution of the (6aR,10aR)-ketone (IV) (0.30 g, 0.95 mmole) in anhydrous methanol (20 mL) was added sodium cyanide (0.30 g, 6.12 mmole) and the mixture stirred at room temperature under argon for 17 hours to give a colorless solution. Glacial acetic acid (0.38 mL) was then added to give a light yellow solution. This was stirred at room temperature for 3 h to give an almost colorless solution. Hydrogen chloride gas was then bubbled in to pH 1 and the reaction mixture, now containing a white precipitate, stirred at room temperature for 24 h, evaporated in vacuo to dryness and the residue partitioned between CH$_2$Cl$_2$ (70 mL) and water (30 mL). The aqueous phase was extracted with more CH$_2$Cl$_2$ (2×30 mL). The combined organic phase was dried (Na$_2$SO$_4$) and evaporated in vacuo to give a 3:2 mixture of the diastereomeric cyanohydrins (VI) and (VII) (335 mg) as an off-white crystalline foam.

A portion of this foam was subjected to preparative TLC on silica (Merck), eluting with CHCl$_3$-MeOH-hexanes (20:10:70) to give the less polar (6aR,9R,10aR)-isomer (VII) as a white foam, $[\alpha]_D$ −106° (CHCl$_3$), (M+H)+ (FAB) 344.2220 (Calc 344.2226); and the more polar (6aR,9S,10aR)-isomer VI also as a white foam, $[\alpha]_D$ −54° (CHCl$_3$), (M+H)+ (FAB) 344.2213 (Calc 344.2226).

EXAMPLE 5

(6aR,9S,10aR)-6a,7,8,9,10,10a-Hexahydro-1,9-dihydroxy-6,6-dimethyl-3-pentyl-6H-dibenzo[b,d]pyran-9-carboxylic acid methyl ester (VIII) and (6aR,9R,10aR)-6a,7,8,9,10,10a-Hexahydro-1,9-dihydroxy-6,6-dimethyl-3-pentyl-6H-dibenzo[b,d]pyran-9-carboxylic acid methyl ester (IX)

With continued reference to scheme 2, to a solution of a mixture of (VI) and (VII) (328 mg, 0.96 mmol) in anhydrous methanol (20 mL) cooled in an ice-bath, was bubbled gaseous hydrogen chloride to saturation for approximately 1 hour. The sealed flask was maintained at 0° C. for 70 h. Hydrochloric acid (6N, 10 mL) was then added, the reaction mixture stirred at room temperature for 16 h and evaporated in vacuo to near dryness. The residue was partitioned between ethyl acetate (EtOAc) (70 mL) and water (40 mL), the aqueous phase saturated with NaCl, the layers separated and the aqueous layer extracted further with EtOAc. The combined organic layers were washed sequentially with water, saturated NaHCO₃ and saturated NaCl, dried (MgSO₄) and evaporated in vacuo to give 343 mg, 95%, of a mixture of (VIII) and (IX) as an off-white foam.

A portion was subjected to preparative TLC on silica (Merck), eluting with CHCl₃-MeOH-hexanes (2:1:7) to give the less polar (6aR,9R,10aR)-isomer (IX) as a glass, $[\alpha]_D - 67°$ (CHCl₃), M+ 376.2257 (Calc 376.2250); and the more polar (6aR,9S,10aR)-isomer (VIII) also as a glass, $[\alpha]_D - 61°$ (CHCl₃), M+ 376.2238 (Calc 376.2250).

EXAMPLE 6

(6aR,10aR)-6a,7,10,10a-Tetrahydro-1-hydroxy-6,6-dimethyl-3-pentyl-6H-dibenzo[b,d]pyran-9-carboxylic acid methyl ester (X)

With continued reference to scheme 2, a solution of triphenylphosphine (1.18 g, 4.5 mmol) and a mixture of (VIII) and (IX) (335 mg, 0.89 mmole) in dry carbon tetrachloride (75 mL) was boiled under reflux and under argon for 18 h. The cooled (room temperature) reaction mixture, now containing triphenylphosphine oxide, was evaporated in vacuo to dryness. The brown-flecked residue was re-dissolved in methanol (100 mL) and stirred at room temperature for 4.5 h, and evaporated in vacuo to dryness. The residue was dissolved in 8 mL of methylene chloride and placed onto the top of a plug of silicagel 60. The silica was washed through with portions of EtOAc-hexanes (3:7) and the fractions containing the product, as shown by TLC on silica, pooled and evaporated in vacuo to give 297 mg, 93%, of crude but fairly pure (X) as an off-white crystalline foam. A sample was further purified by chromatography on silica, carefully eluting with CHCl₃-MeOH-hexanes (2:1:7), to give pure (X) as a white foam, $[\alpha]_D - 283°$ (CHCl₃), M+ 358.2138 (Calc 358.2144).

EXAMPLE 7

(6aR,10aR)-6a,7,10,10a-Tetrahydro-1-hydroxy-6,6-dimethyl-3-pentyl-6H-dibenzo[b,d]pyran-9-carboxylic acid (XI)

With further reference to scheme 2, a solution of (X) (290 mg, 0.81 mmole) in methanol (25 mL) was sparged with argon for 0.5 h. Sodium hydroxide (2N, 20 mL) was sparged with argon and was added and the resulting solution stirred at room temperature for 15 h. The solution was then acidified with 6N HCl to pH 1 and evaporated in vacuo to remove the methanol. Water (10 mL) was added and the aqueous phase extracted three times with ethyl acetate. The combined organic extracts were washed with saturated NaCl, dried over Na₂SO₄ and evaporated in vacuo to give 296 mg of a pale brown foam. Recrystallization of this material from CH₂Cl₂-petroleum ether (30/60) gave 27 mg of white crystals containing most of the impurities. Evaporation of the mother liquors then gave 269 mg of almost pure (XI) as a foam. A sample was further purified by chromatography on silica, eluting with EtOAc-hexanes-MeOH (5:3:2), to give pure (XI), $[\alpha]_D - 286°$ (EtOH) (Mechoulam et al in Experientia, 29:1193 (1973) gives $[\alpha]_D - 287°$ (EtOH)), $[\alpha]_D - 238°$ (CHCl₃), M+ 344.1963 (Calc 344.1988).

EXAMPLE 8

(6aR,10aR)-1-[[(6a,7,10,10a-Tetrahydro-1-hydroxy-6,6-dimethyl-3-pentyl-6H-dibenzo[b,d]pyran-9-yl)carbonyl]oxy]-2,5-pyrrolidinedione (XII)

With further reference to scheme 2, to a solution of (XI) (50 mg, 0.145 mmol) in dry tetrahydrofuran (THF) (4 mL) under argon, was added dicyclohexylcarbodiimide (Aldrich; 120 mg, 0.58 mmol) and N-hydroxysuccinimide (Aldrich; 102 mg, 0.89 mmol). The solution was stirred at room temperature for 1 hr and then at 40° C. for 3 h after which TLC on silica indicated no starting material was left. The reaction mixture was cooled to room temperature, the crystalline precipitate of dicyclohexylurea filtered off, and the filtrate evaporated in vacuo to give a solidifying gum. Preparative TLC on silica, eluting with EtOAc-hexanes (1:1) then gave 57 mg of a solid material isolated from the main band, shown by ¹H NMR to contain 44 mg, 69%, of the NHS ester (XII) together with 13 mg of dicyclohexylurea. This mixture was used without further purification in the preparation of the compound (XXI) (tracer Ic) as described in Example 14.

In an alternate approach, 2 equivalents of 1-(3-dimethylaminopropyl)-3-ethylcarbodiimide hydrochloride (EDC-HCl) as the coupling reagent in the reaction of (XI) were mixed with 1.5 equivalents of N-hydroxysuccinimide in CH₂Cl₂ at reflux for 24 h. Dilution of the resulting reaction mixture with EtOAc, washing with water, saturated NaHCO₃, saturated NaCl, drying over Na₂SO₄ and evaporation in vacuo then gave a gum. This was subjected to chromatography on silica, eluting with EtOAc-hexanes (1:1) to give (XII) as an off-white foam, $[\alpha]_D - 208°$ (CHCl₃), (M+H)+ (FAB) 442.2260 (Calc 442.2230).

EXAMPLE 9

(6aS,9S,10aS)-6a,7,8,9,10,10a-Hexahydro-1,9-dihydroxy-6,6-dimethyl-3-pentyl-6H-dibenzo[b,d]pyran-9-carbonitrile (XIII) and (6aS,9R,10aS)-6a,7,8,9,10,10a-hexahydro-1,9-dihydroxy-6,6-dimethyl-3-pentyl-6H-dibenzo[b,d]pyran-9-carbonitrile (XIV)

Referring to scheme 3, by the same procedure as described for compounds (VI) and (VII) in Example 4, reaction of the 6aS,10aS-ketone (V) (100 mg, 0.316 mmol) with NaCN (100 mg, 2.04 mmol) in dry methanol (5 mL) and work-up as previously described, gave 103 mg, 95%, of a 3:2 mixture of (XIII) and (XIV) as an off-white crystalline foam, (M+H)+ (FAB) 344.2229 (Calc 344.2226).

EXAMPLE 10

(6aS,9S,10aS)-6a,7,8,9,10,10a-Hexahydro-1,9-dihydroxy-6,6-dimethyl-3-pentyl-6H-dibenzo[b,d]pyran-9-carboxylic acid methyl ester (XV) and (6aS,9R,10aS)-6a,7,8,9,10,10a-hexahydro-1,9-dihydroxy-6,6-dimethyl-3-pentyl-6H-dibenzo[b,d]pyran-9-carboxylic acid methyl ester (XVI)

With continued reference to scheme 3, application of the same method as described for preparation of (VIII) and (IX) in Example 5, to the reaction of the mixture of (XIII) and (XIV) (100 mg, 0.291 mmol) in methanol (5 mL) saturated with HCl (gas) for 4 days gave, after work-up, 107 mg, 98% crude yield, of a mixture of (XV) and (XVI) as an off-white foam.

Further purification of a portion of this material by preparative TLC on silica, eluting carefully with hexanes-CHCl₃-MeOH (75:20:5), then gave the (6aS,9S,10aS)-isomer (XV) from the less polar band as a white foam, $[\alpha]_D + 67°$ (CHCl₃), M+ 376.2233 (Calc 376.2250); and the (6aS,9R,10aS)-isomer (XVI) from the more polar band also as a white foam, $[\alpha]_D + 66°$ (CHCl$_3$), M+ 376.2234 (Calc 376.2250).

EXAMPLE 11

(6aS,10aS)-6a,7,10,10a-Tetrahydro-1-hydroxy-6,6-dimethyl-3-pentyl-6H-dibenzo[b,d]pyran-9-carboxylic acid methyl ester (XVII)

Following the same method described for preparing (X) and following scheme 3, and Example 6, reaction of a mixture of (XV) and (XVI) (101 mg, 0.268 mmol) with triphenylphosphine (Aldrich; 352 mg, 1.34 mmol) in carbon tetrachloride (10 mL) at reflux for 16 h gave after work-up 91 mg, 95%, of the ester (XVII) as a white foam. A sample was further purified by preparative TLC on silica, eluting carefully with hexanes-CHCl$_3$-MeOH (75:20:5) to give pure (XVII) as a white foam, $[\alpha]_D + 298°$ (CHCl$_3$), M+ 358.2169 (Calc. 358.2144).

EXAMPLE 12

(6aS,10aS)-6a,7,10,10a-Tetrahydro-1-hydroxy-6,6-dimethyl-3-pentyl-6H-dibenzo[b,d]pyran-9-carboxylic acid (XVIII)

By the same procedure described before for preparing (XI) in Example 7, hydrolysis of the (6aS,10aS)-ester (XVII) (22 mg, 0.061 mmol) with argon sparged 2N NaOH (3 mL) in argon sparged methanol (4 mL) at room temperature for 18 h gave, after work-up, 22 mg of a gum. This was subjected to preparative TLC on silica, eluting with hexanes-CHCl$_3$-MeOH (7:2:1) to give, from the main band, 16 mg, 76%, of the (6aS,10aS)-acid (XVIII) as a glass, $[\alpha]_D + 310°$ (CHCl$_3$), M+ 344.1983 (Calc 344.1988).

EXAMPLE 13

(6aS,10aS)-1-[[(6a,7,10,10a-Tetrahydro-1-hydroxy-6,6-dimethyl-3-pentyl-6H-dibenzo[b,d]pyran-9-yl)carbonyl]oxy]-2,5-pyrrolidinedione (XIX)

With reference to scheme 3, to a solution of (XVIII) (6 mg, 0.017 mmol) in dry THF (2 mL), under argon, was added dicyclohexylcarbodiimide (Aldrich; 13 mg, 0.063 mmol) and N-hydroxysuccinimide (Aldrich; 11 mg, 0.096 mmol). The resulting reaction mixture was stirred for 43 h, filtered from dicyclohexylurea, and the filtrate evaporated in vacuo to afford white solids. This material was digested with a small volume of THF and the insoluble part (urea) was filtered off. The filtrate was evaporated in vacuo to dryness and the process repeated to give a foam which was subjected to preparative TLC on silica, eluting with EtOAc-hexanes (1:1), to give 5 mg, 67%, of the NHS ester as an off-white foam.

EXAMPLE 14

(6aR,10aR)-N-[3-[[(6a,7,10,10a-Tetrahydro-1-hydroxy-6,6-dimethyl-3-pentyl-6H-dibenzo[b,d]pyran-9-yl)carbonyl]amino]-2-hydroxypropyl]-3',6'-dihydroxy-3-oxospiro[isobenzofuran-1(3H),9'-[9H]xanthene]-5-carboxamide (XXI) (Tracer Ic)

With reference to scheme 4a, to a solution of the NHS ester (XII) (57 mg of a mixture comprising 44 mg, 0.01 mmol, of (XII) and 13 mg of dicyclohexylurea) in dry pyridine (5 mL) was added 1,3-diamino-2-hydroxypropane (Aldrich; 100 mg, 1.11 mmol) and the solution then stirred at room temperature for 17 h under argon. The clear solution was evaporated in vacuo to dryness and then partitioned between diethyl ether (100 mL) and water (30 mL). The phases were separated and the aqueous phase extracted with two further portions of diethyl ether. The combined organic phases were washed with saturated NaCl (30 mL), dried over Na$_2$SO$_4$, evaporated in vacuo and the residue thus obtained was placed under vacuum (0.2 torr) at room temperature for 3 h to give 52 mg of crude (XX), still containing dicyclohexylurea by $^1$H NMR, as a glass.

This material was re-dissolved in dry pyridine (5 mL) and 5-carboxyfluorescein N-hydroxysuccinimide ester (Research Organics; 48 mg, 0.10 mmol) added in one lot to the stirred reaction mixture. After 16 h at room temperture under argon, the clear yellow-orange solution was evaporated in vacuo to dryness to give an orange gum which was re-dissolved in methanol (1 mL) and purified by preparative TLC on silica, eluting with CHCl$_3$-MeOH (65:35). The main orange, fluorescent band was removed from the plate and the silica washed with CHCl$_3$-MeOH (1:1). The washings were evaporated in vacuo to give an orange solid. This was resubjected to preparative TLC on silica, eluting with CHCl$_3$-MeOH (85:15), to give from the main band an orange material which was resubjected again to preparative TLC on analytical grade silica, eluting with CHCl$_3$-MeOH (65:35). The product band was isolated from the plates and the silica eluted with CHCl$_3$-MeOH (1:1) and the eluate evaporated in vacuo to give an orange solid. This was taken up in CHCl$_3$-MeOH (95:5), filtered through a 0.5 micron filter, the filtrate evaporated in vacuo and the residue placed under vacuum (0.2 torr) at room temperature with protection from light to afford 47 mg, 61%, of (XXI) (tracer Ic) as a flaky, deep orange solid: mp>330° C. (decomposes); $[\alpha]_D - 108°$ (MeOH); and (M+H)+ (FAB) 775.3288 (Calc 775.3231).

EXAMPLE 15

(6aS,10aS)-N-[3-[[(6a,7,10,10a-Tetrahydro-1-hydroxy-6,6-dimethyl-3-pentyl-6H-dibenzo[b,d]pyran-9-yl)carbonyl]amino]-2-hydroxypropyl]-3',6'-dihydroxy-3-oxospiro[isobenzofuran-1(3H),9'-[9H]xanthene]-5-carboxamide (XXIII) (Tracer If)

Referring to scheme 4b, in a similar manner to the preparation of (XXI) in Example 14, reaction of the (6aS,10aS)-ester (XIX) (5 mg of a mixture comprising 3 mg, 0.007 mmol, of (XIX) and 2 mg of dicyclohexylurea) with 1,3-diamino-2-hydroxypropane (Aldrich; 12 mg, 0.133 mmol) in dry pyridine (1 mL) at room temperature for 15 h under argon gave, after work-up, 4.5 mg of crude (XXII) as a colorless glass. This was re-dissolved in dry pyridine (1 mL) and to the stirred solution was added 5-carboxyfluorescein N-hydroxysuccinimide ester (Research Organics; 5 mg, 0.011 mmol). After 15 h stirring at room temperature the clear yellow-orange solution was evaporated in vacuo and the residue subjected to multiple chromatographic purifications as described before to give 4 mg, 74%, of the (6aS,10aS)-tracer (XXIII) (tracer If) as deep orange flakes: mp>330° C. (decomposes); $[\alpha]_D + 114°$ (MeOH); (M+H)+ (FAB) 775.3249 (Calc 775.3231).

EXAMPLE 16

(trans-racemic)-6a,7,10,10a-Tetrahydro-1-[3-[[(3',6'-di hydroxy-3-oxospiro[isobenzofuran-1(3H),9'-[9H]xanthen-5-yl]carbonyl]amino]propoxy]-6,6-dimethyl-3-pentyl-6H-dibenzo[b,d]pyran-9-carboxylic acid (XXVIII)

To a solution of (trans-racemic)-1-(3-aminopropoxy)-6a,7,10,10a-tetrahydro-6,6-dimethyl-3-pentyl-6H-dibenzo[b,d]pyran-9-carboxylic acid monohydrochloride (XXVII); 108 mg, 0.247 mmol; (McNally, et. al., U.S. Pat. No. 4,833,073) in dry pyridine (10 mL) containing dry triethylamine (0.04 mL, 1.1 eq) was added 5-carboxyfluorescein N-hydroxysuccinimide ester (Research Organics; 116 mg, 0.245 mmol). The reaction solution was then stirred at room temperature for 9 h under argon after which thin layer chromatography on silica, eluting with $CHCl_3$-MeOH (75:25) indicated some (XXVII) remained. A further addition, 5 mg, 0.01 mmol, of the fluorescein compound was added, followed by a further 10 mg, 0.02 mmol, of this fluorescein compound after an additional 14th stirring together with an additional 3 mL of triethylamine. After stirring for an additional 16.5 h the reaction mixture was evaporated in vacuo to dryness and the resulting orange oil subjected to preparative TLC on silica, eluting with $CHCl_3$-MeOH (75:25). The main orange colored, fluorescent band was isolated from the plate, the silica eluted with $CHCl_3$-MeOH (1:1) and the washings evaporated in vacuo to afford 147 mg, 79% crude yield, of (XXVIII) as an orange solid. This was resubjected to preparative TLC as above to give, from the product band, 126 mg, 67%, of purified (XXVIII) as a yellow-orange solid: $(M+H)^+$ (FAB) 760.3136 (Calc 760.3122); Anal. Calc for $C_{45}H_{45}NO_{10}.3H_2O$: C, 66.41; H, 6.32; N, 1.72. Found: C, 66.63; H, 5.87; N, 1.80%.

EXAMPLE 17

Preparation of tracers Ia, Id–Ie, Ig–Ii (trans-racemic)-1-[[(6a,7,10,10a-Tetrahydro-1-hydroxy-6,6-dimethyl-3-pentyl-6H-dibenzo[b,d]pyran-9-yl)carbonyl]oxy]-2,5-pyrrolidinedione (XXIV) was obtained by reacting the corresponding (trans-racemic)-6a,7,10,10a-tetrahydro-1-hydroxy-6,6-dimethyl-3-pentyl-6H-dibenzo[b,d]pyran-9-carboxylic acid (Schwartz & Madan, J. Org. Chem., 1986, 51, 5463) with N-hydroxysuccinimide using dicyclohexylcarbodiimide or 1-(3-dimethylaminopropyl)-3-ethylcarbodiimide as coupling agent. Compound (XXIV) was reacted with from 1.1 to 10 equivalents of the corresponding diamino linker compound in pyridine solution followed by, with or without isolation of the intermediate compound, subsequent reaction of this intermediate with 1 to 1.1 equivalents of 5-carboxyfluorescein N-hydroxysuccinimide ester (Research Organics; 5-carboxyfluorescein NHS ester) in pyridine solution at room temperature typically for 14 h to 18 h. The reaction mixture was then evaporated in vacuo, the residue re-dissolved in methanol and applied to preparative TLC silica plates. After development with a suitable solvent or solvent mixture (for example, 1:3 MeOH-$CHCl_3$) the product bands were removed from the plates and the silica eluted with a solvent or solvent mixture more polar than the developing solvent, (for example, 1:1 MeOH-$CHCl_3$). Evaporation in vacuo of the washings then gave the tracers which were typically purified further by repeating the process above.

(trans-racemic)-1-[[(6a,7,8,10a-Tetrahydro-1-hydroxy-6,6-dimethyl-3-pentyl-6H-dibenzo[b,d]pyran-9-yl)carbonyl]oxy]-2,5-pyrrolidinedione (XXXV) was obtained by reacting the corresponding (trans-racemic)-acid (XXXII) with N-hydroxysuccinimide using 1-(3-dimethylaminopropyl)-3-ethylcarbodiimide as coupling agent.

Tracer Ia is obtained from XXIV by reaction with 2,3-diaminopropionic acid in pyridine-pH 8 buffer, followed by reaction with 5-carboxyfluorescein NHS ester as described above.

Tracer Id is obtained from (XXXV) in a similar manner to the above general procedure. Tracer Ie is obtained from (XXXV) in a similar manner to the above general procedure but using 6-carboxyfluorescein NHS ester (Research Organics) instead. Reaction schemes for Tracers Id and Ie are shown in Scheme 5.

Tracer Ii was made from (XXIV) following the above general procedure and in a manner corresponding to Example 14.

In the case of Tracer Ig, the intermediate compound was formed from reaction of (XXIV) and the corresponding $N\epsilon$-$^t$BOC protected L-lysine followed by deprotection of the $\epsilon$-amino before reaction with 5-carboxyfluorescein NHS ester using conventional methods.

In the case of Tracer Ih, the $N\alpha$-$^t$BOC L-lysine was reacted with (XXIV) to give the intermediate compound. Deprotection of the $\alpha$-amino and reaction with 5-carboxyfluorescein NHS ester following conventional methods then afforded the tracer.

EXAMPLE 18

Preparation of Tracers Ib, Ik and Im

These tracers were prepared by a method analogous to that of Example 17 except that the corresponding intermediate compounds were reacted with 5-isothiocyanatofluorescein instead of 5-carboxyfluorescein NHS ester.

EXAMPLE 19

Preparation of Tracers Ij and Il

These tracers were prepared by the general method of Example 17 except that the corresponding intermediate compound was reacted with 5-isocyanatofluorescein, generated in situ from 5-aminofluorescein and phosgene in the presence of triethylamine.

EXAMPLE 20

Fluroescence Polarization Immunoassay Using Tracers Of The Invention

Assay Reagents and Protocols, as performed on the automated COBAS TM FARA (Roche Diagnostic Systems Inc., Branchburg, N.J., a subsidiary of Hoffmann-La Roche Inc., Nutley, N.J.) machine configured for fluorescence polarization measurements for cannabinoids in a urine sample:

i) Reagents Formulations:

a) Cannabinoid Metabolite Antibody Reagent: 0.1M Tris pH 8.0 containing 0.2% azide, 1% ethylene glycol, 0.05% riboflavin binding protein (RBP), 0.25% naphthalene-1-sulfonate, and a suitable dilution of antibody specific for cannabinoids.

b) Cannabinoid Tracer Reagent: 0.1M ACES pH 8.0 containing 0.2% azide, 0.01% bovine gamma globulin (BGG), $1.26 \times 10^{-7}$M in tracer, $(1.66 \times 10^{-2})$ % lithium dodecyl sulfate (LDS), 0.77% alpha cyclodextran (from American Maize-Products Company, Hammond, Ind.), and 0.062% EDTA.

c) Cannabinoid Metabolite Calibrators:

For a 25 ng/mL cut-off level assay: Solutions of 0, 6.25, 12.5, 25, 37.5 and 50 ng/mL of $\Delta^9$-11-nor-9-carboxytetrahydrocannabinol in a buffer containing 0.1M ACES pH 8.0 containing 0.2% azide, 0.01% BGG, $(1.66 \times 10^{-2})$% lithium dodecyl sulfate, 0.77% alpha cyclodextran, and 0.062% EDTA; or urine containing 0.2% azide.

For a 50 ng/mL cut-off level assay: Solutions of 0, 12.5, 25, 50, 75 and 100 ng/mL of $\Delta^9$-11-nor-9-carboxytetrahydrocannabinol in a buffer containing 0.1M ACES pH 8.0 containing 0.2% azide, 0.01% BGG, $(1.66 \times 10^{-2})$% lithium dodecyl sulfate, 0.77% alpha cyclodextran, and 0.062% EDTA; or urine containing 0.2% azide.

For a 100 ng/mL cut-off level assay: Solution of 0, 25, 50, 100, 150 and 200 ng/mL of $\Delta^9$-11-nor-9-carboxytetrahydrocannabinol in a buffer containing 0.1M ACES pH 8.0 containing 0.2% azide, 0.01% BGG, $(1.66 \times 10^{-2})$% lithium dodecyl sulfate, 0.77% alpha cyclodextran, and 0.062% EDTA; or urine containing 0.2% azide.

d) Cannabinoid Metabolite Controls: Solutions of 18.75 and 31.25 ng/mL of $\Delta^9$-11-nor-9-carboxytetrahydrocannabinol in urine containing 0.001% LDS and 0.2% azide.

ii) Assay Protocol:
a) For FARA:
1. Antibody reagent: 200 μL
2. Tracer reagent: 30 μL
3a. Sample (with polyclonal Ab): 10 μL* or 18 μL#
3b. Sample (with monoclonal Ab): 22 μL@
Mix 1 and 3: read background; add 2; incubate 30 sec. Read fluorescence polarization.
KEY: *: 50 ng/mL cut-off assay, #: 100 ng/mL cut-off assay, @: 25 ng/mL cut-off assay.

b) A standard curve is obtained using the above-described calibrators as the "sample."

c) The urine specimens or unknown specimens are used as the "sample" and the readings of the fluorescence polarization are compared against the standard curve to give the concentrations of cannabinoids in the sample.

The above steps (a) to (c) are automated steps performed on the previously indicated instruments.

EXAMPLE 21

Comparison of Carbamazepine Tracers

A comparison was made between two tracer compounds identical in structure except that one tracer contained a hydroxy substituent on the linking group, and were performed with different antibodies. It is important to note that the span and intensity of each tracer was compared at the same concentration in the presence of antibody at the same titer (dilution) in each individual case. Measurements were made using conventional FPIA techniques. The results are displayed in the following Table I.

TABLE I

| ANTIBODY # | SPAN | INTENSITY | SPAN | INTENSITY |
|---|---|---|---|---|
| 1. titer = 1/400 | 111 | 0.44 | 102 | 0.23 |
| 2. titer = 1/100 | 59 | 0.84 | 48 | 0.54 |
| 3. titer = 1/1200 | 71 | 0.74 | 71 | 0.55 |
| 4. titer = 1/400 | 64 | 0.73 | 48 | 0.55 |
| 5. titer = 1/100 | 49 | 0.84 | 19 | 0.71 |

[Fl$^5$] = 5-fluoresceinyl

The results in Table I show that in all cases the observed fluorescense intensity (in the absence of added sample or calibrators containing carbamazepine) of the tracer bearing the hydroxy substituent on the linker is higher than that of the tracer without the hydroxy substituent. Use of the hydroxy substituted tracer thus provides a desirable higher signal-to-noise ratio. When the tracer is then allowed to compete with increasing concentrations of added carbamazepine calibrator (from 0 to 20 μg/mL) for binding to antibody, the fall in observed fluorescence polarization (the span) is greater in the case of the tracer bearing the hydroxy substituent on the linker over the tracer without the hydroxy substituent. This greater span results in a wider dynamic range for the assay and allows for greater precision when the tracer bearing the hydroxy substituent is utilized in the assay for carbamazepine.

EXAMPLE 22

Comparison of tetrahydrocannabroid tracers

A comparison was made between matched sets of tetrahydrocannbinoid tracers with or without polar hydrophilic substituents of the linking groups. The relative fluorescent brightness of the tracers were measured by FPIA, and are shown in Table II.

TABLE II $$F-Y-\overset{\overset{O}{\|}}{C}-NH-Z-NH-\overset{\overset{O}{\|}}{C}-X \qquad I$$

| F | Y | Q | Z | X | Relative Brightness |
|---|---|---|---|---|---|
| 5-fluoresceinyl (Tracer Ia) | Single bond | oxygen | carboxyethylene | $\Delta^8$-THC | 1.33 |
| 5-fluoresceinyl (Tracer Ii) | single bond | oxygen | hydroxypropylene | $\Delta^8$-THC | 1.31 |
| 5-fluoresceinyl | single bond | oxygen | ethylene | $\Delta^8$-THC | 0.88 |
| 5-fluoresceinyl (Tracer Ib) | —NH— | sulfur | carboxyethylene | $\Delta^8$-THC | 1.04 |
| 5-fluoresceinyl | —NH— | sulfur | ethylene | $\Delta^8$-THC | 0.614 |

EXAMPLE 23

Comparison of Phenytoin Tracers

A comparison was made between two tracer compounds identical in structure except that one tracer contained a hydroxy substituent on the linking group, and was performed with different antibodies. The span and intensity of each tracer was compared at the same concentration of tracer in the presence of antibody at the same titer (dilution) in each individual case. Measurements were made using conventional FPIA techniques. The results are displayed in Table 3.

TABLE III

| ANTIBODY # | SPAN | INTENSITY | SPAN | INTENSITY |
|---|---|---|---|---|
| 1. titer = 1/275 | 99 | 1.50 | 88 | 1.31 |
| 2. a. titer = 1/250 | 156 | 0.77 | 122 | 0.81 |
| b. titer = 1/190 | 170 | 0.62 | 134 | 0.60 |
| 3. titer = 1/300 | 119 | 1.69 | 118 | 1.59 |

[Fl$^5$] = 5-fluoresceinyl.
Span is in mP units.
Intensity is in relative units.

The results in Table 3 show that in all cases the observed fluorescence intensity (at zero concentration of phenytoin calibrators or standards) of the tracer bearing the hydroxy substituent on the linking group is either about the same or higher than that of the tracer without the hydroxy substituent. When the tracer is then allowed to compete with increasing concentrations of added phenytoin calibrator (from 0 to 40 µg/mL) for binding to antibody, the fall in observed fluorescence polarization is about the same or greater in the cases for the tracer bearing the hydroxy substituent on the linker, over the tracer without the hydroxy substituent. In the case with Antibody #1 both the span and tracer intensity is greater for the tracer with the hydroxy substituent on the linking group. In a similar manner to the cases described in Example 21, the above results allow the formulation of an assay for phenytoin characterized by greater precision and/or with a greater signal-to-noise ratio when the tracer bearing the hydroxy substituent on the linking group is utilized, rather than the tracer without the hydroxy substituent.

What is claimed is:

1. A compound of the formula:

$$F-Y-\overset{\overset{O}{\|}}{C}-NH-Z-NH-\overset{\overset{O}{\|}}{C}-X \qquad I$$

wherein F is a fluorescent group; Y is —NH— or a single covalent bond; Z is straight or branched alkylene chain of two to ten carbon atoms which is substituted with at least one hydrophilic group; Q is oxygen or sulfur; and X is a ligand-analog capable of being recognized by an antibody specific to the corresponding ligand.

2. The compound according to claim 1, wherein X is a tetrahydrocannabinoid analog.

3. The compound according to claim 1, wherein X is a carbamazepine analog.

4. The compound according to claim 1, wherein X is a phenytoin analog.

5. The compound according to claim 1, wherein the polar hydrophilic group is selected from the group consisting of hydroxy, carboxy, carboxylate esters, carbamyl, thiocarbamyl, amino, substituted amino, sulfino, sulfo, sulfamyl, phosphono, nitro, hydroxyalkoxy, or aminoalkoxy.

6. The compound according to claim 2, wherein Y is a single covalent bond; Q is oxygen; and Z is 2-hydroxy propylene.

7. The compound according to claim 2, wherein Y is —NH—, and Q is oxygen.

8. The compound according to claim 5, wherein the tetrahydrocannabinoid analog is 6a,7,10,10a-tetrahydro-1-hydroxy-6,6-dimethyl-3-pentyl-6H-dibenzo[b,d]-pyran-9-yl.

9. The compound according to claim 5, wherein the tetrahydrocannabinoid analog is 6a,7,8,10a-tetrahydro-1-hydroxy-6,6-dimethyl-3-pentyl-6H-dibenzo[b,d]pyran-9-yl.

10. The compound according to claim 1, wherein F is 5-fluoresceinyl.

11. The compound according to claim 1, wherein F is 6-fluoresceinyl.

12. The compound according to claim 6, wherein F is 5-fluoresceinyl.

13. The compound according to claim 6, wherein F is 6-fluoresceinyl.

* * * * *

UNITED STATES PATENT AND TRADEMARK OFFICE
CERTIFICATE OF CORRECTION

PATENT NO. : 5,315,015

DATED : May 24, 1994

INVENTOR(S) : Raymond Albert Hui and Kathryn Sarah Schwenzer

It is certified that error appears in the above-identified patent and that said Letters Patent is hereby corrected as shown below:

In column 1, lines 59-63, please delete the chemical formula and insert therefore --  I --.

In column 2, lines 17-21, please delete the chemical formula and insert therefore --  I --.

In the claims:

In claim 1, lines 17-21, column 32, please delete the chemical formula and insert therefore -- 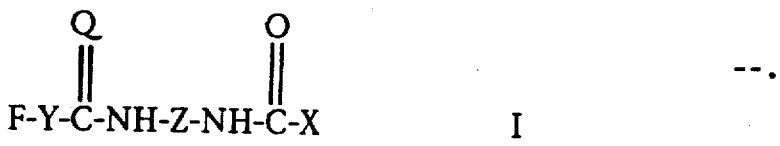 I --.

In the abstract:

On the front page of the Patent, in section 57 ABSTRACT, please delete the chemical formula and insert therefore -- 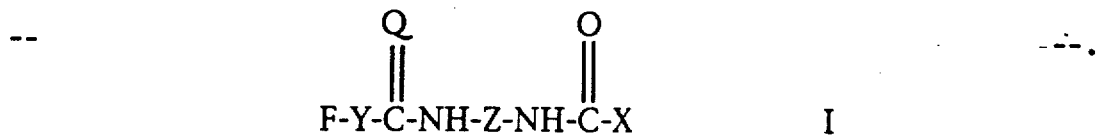 I --.

UNITED STATES PATENT AND TRADEMARK OFFICE
CERTIFICATE OF CORRECTION

PATENT NO. : 5,315,015
DATED : May 24, 1994
INVENTOR(S) : Raymond Albert Hui and Kathryn Sarah Schwenzer It is certified that error appears in the above-identified patent and that said Letters Patent is hereby corrected as shown below:

*Columns 5 and 6, please delete the second chemical formula labeled "Tracer Ib", and insert the following:

--

Tracer Ib

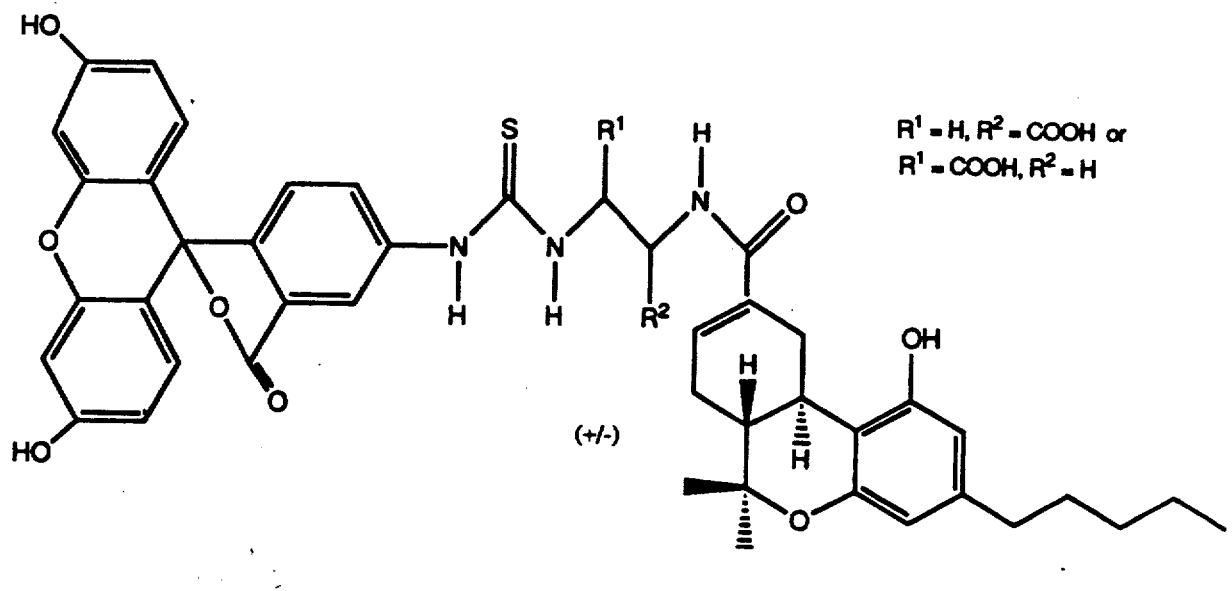

$R^1 = H$, $R^2 = COOH$ or
$R^1 = COOH$, $R^2 = H$

--.

UNITED STATES PATENT AND TRADEMARK OFFICE
CERTIFICATE OF CORRECTION

PATENT NO. : 5,315,015

DATED : May 24, 1994

INVENTOR(S) : Raymond Albert Hui and Kathryn Sarah Schwenzer

It is certified that error appears in the above-identified patent and that said Letters Patent is hereby corrected as shown below:

*Columns 9 and 10, please delete the fourth chemical formula labeled "Tracer II", and insert the following:

--

Tracer II

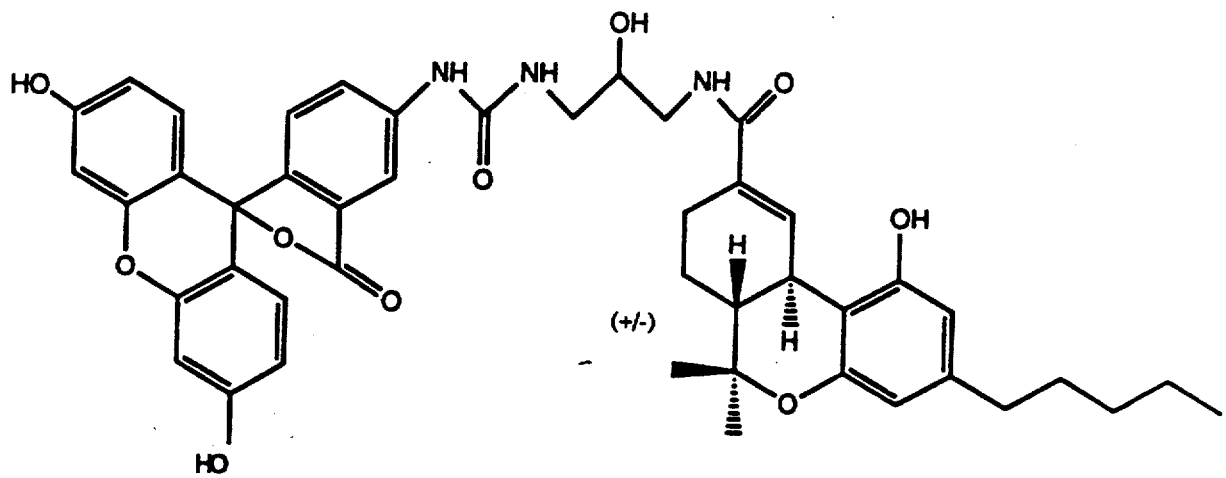

--.

UNITED STATES PATENT AND TRADEMARK OFFICE
CERTIFICATE OF CORRECTION

PATENT NO. : 5,315,015

DATED : May 24, 1994

INVENTOR(S) : Raymond Albert Hui and Kathryn Sarah Schwenzer

It is certified that error appears in the above-identified patent and that said Letters Patent is hereby corrected as shown below:

Columns 19 and 20, please delete the last chemical formula in Scheme 5 and insert the following:

--

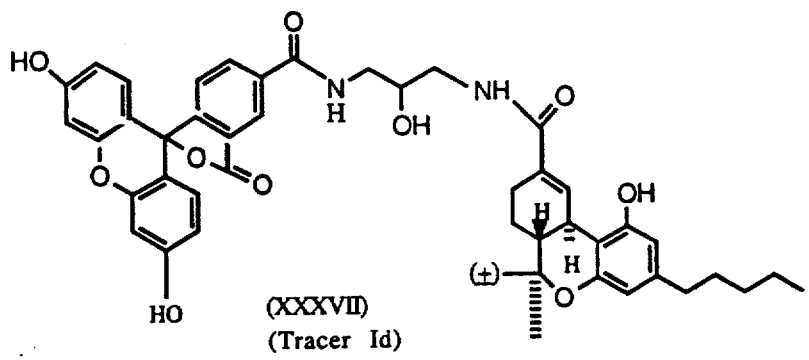

(XXXVII)
(Tracer Id)

--.

Column 30, line 62, please delete "tetrahydrocannabroid" and insert therefor -- tetrahydrocannabinoid --.

Signed and Sealed this

Twentieth Day of September, 1994

Attest:

BRUCE LEHMAN

Attesting Officer

Commissioner of Patents and Trademarks